United States Patent [19]

Evans

[11] Patent Number: 4,670,495
[45] Date of Patent: Jun. 2, 1987

[54] O-LINKED POLYPHENOLIC ANTIOXIDANTS

[75] Inventor: Samuel Evans, Marly, Switzerland

[73] Assignee: Ciba-Geigy Corporation, Ardsley, N.Y.

[21] Appl. No.: 878,402

[22] Filed: Jun. 20, 1986

Related U.S. Application Data

[63] Continuation of Ser. No. 807,194, Dec. 9, 1985, abandoned, which is a continuation of Ser. No. 741,089, Jun. 4, 1985, abandoned, which is a continuation of Ser. No. 641,093, Aug. 15, 1984, abandoned.

[30] Foreign Application Priority Data

Aug. 24, 1983 [CH] Switzerland .................... 4617/83

[51] Int. Cl.$^4$ .................. C07C 147/10; C07C 147/14; C07C 149/40; C07C 69/675; C08K 5/13; C08K 5/36; C08K 5/41

[52] U.S. Cl. ..................................... 524/155; 524/171; 524/291; 524/331; 524/332; 524/342; 560/70; 560/75; 568/23; 568/27; 568/47; 568/720

[58] Field of Search ............... 524/155, 171, 291, 331, 524/332, 342; 568/23, 27, 47, 720; 560/70, 75

[56] References Cited

U.S. PATENT DOCUMENTS

| | | | |
|---|---|---|---|
| 2,822,404 | 2/1958 | Ambelang ........................... | 524/342 |
| 3,392,141 | 7/1968 | Blumberg et al. .................... | 560/75 |
| 3,506,716 | 4/1970 | Peterli ................................. | 260/609 |
| 3,960,929 | 6/1976 | Mauz .................................. | 524/291 |
| 3,986,981 | 10/1976 | Lyons ................................. | 252/404 |
| 4,009,147 | 2/1977 | Lyons ................................. | 260/609 |
| 4,101,511 | 7/1978 | Floyd et al. ......................... | 524/171 |
| 4,136,055 | 1/1979 | Lyons ................................. | 252/404 |
| 4,248,804 | 2/1981 | Yamaguchi et al. ................ | 524/332 |

FOREIGN PATENT DOCUMENTS

| | | |
|---|---|---|
| 1092026 | 11/1960 | Fed. Rep. of Germany . |
| 2500576 | 11/1975 | Fed. Rep. of Germany . |
| 1102557 | 2/1968 | United Kingdom . |
| 524823 | 12/1976 | U.S.S.R. . |

OTHER PUBLICATIONS

CA 84 60571f (1976).

Primary Examiner—Veronica P. Hoke
Attorney, Agent, or Firm—Luther A. R. Hall

[57] ABSTRACT

Novel o-bridged polynuclear polyphenols of the formula I

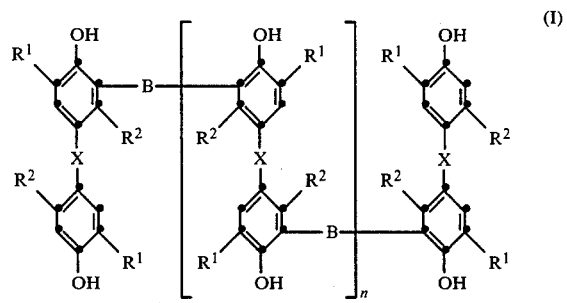

which contain at least one organic radical, such as alkyl, cycloalkyl or aryl, per phenyl nucleus and are formed by condensation of the monomeric phenolic components with customary bridging reagents, such as formaldehyde, acetone or sulfur dichloride, or by oxidative coupling of the monomeric phenolic components, and which, depending on the reaction procedure, can contain between 2 and 50 monomer units, are described.

The substances according to the invention can be used for stabilizing plastics from oxidative degradation and have a good resistance to extraction.

16 Claims, No Drawings

O-LINKED POLYPHENOLIC ANTIOXIDANTS

This is a continuation of application Ser. No. 807,194, filed Dec. 9, 1985, now abandoned, which in turn is a continuation of application Ser. No. 741,089, filed June 4, 1985, now abandoned, which in turn is a continuation of application Ser. No. 641,093, filed Aug. 15, 1984, now abandoned.

The present invention relates to novel high molecular weight o-linked polyphenols which can be used as anti-oxidants in polymers, and the organic material thereby stabilised.

The use of high molecular weight polyphenols as anti-oxidants is known. Thus, according to German Offenlegungsschrift No. 2,500,576, oligomeric polyphenols are obtained by linking monomeric phenolic units—in this case hydroxybiphenyls—via sulfide bridges.

When these substances are incorporated into polymeric organic materials together with carbon black, a synergistic intensification of the heat stabilisation is obtained.

U.S. Pat. No. 3,986,981 describes anti-oxidative oligomeric polyphenols which are linked via direct C—C bonds and are obtained by oxidative coupling of bis-phenols.

The present invention relates to compounds of the formula I

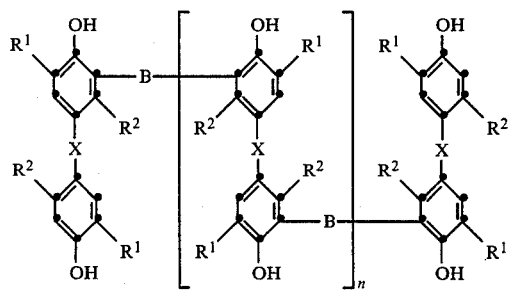

in which $R^1$ is $C_1$–$C_{12}$-alkyl, $C_5$–$C_7$-cycloalkyl, phenyl, 1-naphthyl, 2-naphthyl or $C_7$–$C_9$-aralkyl, $R^2$ is either hydrogen or methyl and X is one of the groups —$(CH_3)C[—(CH_2)_m$—CO—$OR^3]$—, —$(CH_3)C(R^4)$—, —SO—, —$SO_2$—, —CH[—$CH_2$—CH($R^5$)($SR^6$)]—, —CH[—$CH_2$—CH($R^5$)(SO—$R^6$)]— or —CH[—$CH_2$—CH($R^5$)($SO_2$—$R^6$)]—, in which $R^3$ is straight-chain or branched $C_1$–$C_{24}$-alkyl, $R^4$ is hydrogen or straight-chain or branched $C_1$–$C_{12}$-alkyl, $R^4$ only being hydrogen or methyl if B is a direct C—C bond, m is 1 or 2 and $R^5$ is hydrogen or methyl, and in which $R^6$ is straight-chain or branched $C_1$–$C_{18}$-alkyl or a group —$(CH_2)_t$—CO—$OR^7$, in which the index t can assume the value 1 or 2 and $R^7$ is straight-chain or branched $C_1$–$C_{18}$-alkyl, and in which, finally, the bridge member B is a direct C—C bond or a group—$(R^8)C(R^9)$—, —S— or —S—S—, in which the substituents $R^8$ and $R^9$ independently of one another are hydrogen, $C_1$–$C_8$-alkyl or phenyl, and in which n can assume the value of a whole number from 0 to 50.

A $C_1$–$C_{12}$-alkyl radical $R^1$ or $R^4$ is, for example, methyl, ethyl, n-propyl, isopropyl, n-butyl, sec.-butyl, tert.-butyl, n-amyl, isoamyl, n-hexyl, n-octyl, 1,1,3,3-tetramethylbutyl, n-decyl, n-dodecyl or 1,1,3,3,5,5-hexamethylhexyl. A $C_5$–$C_7$-cycloalkyl radical $R^1$ is, for example, cyclopentyl, cyclohexyl or cycloheptyl. However, the particularly preferred $C_1$–$C_8$-alkyl radical $R^1$ is methyl or tert.-butyl. $R^4$ is preferably methyl.

A $C_7$–$C_9$-aralkyl radical $R^1$ can be, for example, benzyl, phenethyl or α,α-dimethylbenzyl.

A —$(CH_3)C[—(CH_2)_m$—CO—$OR^3]$— group X can be, for example, one of the radicals —$(CH_3)C[—CH_2$—CO—$OCH_3]$—, —$(CH_3)C[—CH_2$—CO—$OC_{18}H_{37}]$— or —$(CH_3)C[—CH_2$—$CH_2$—CO—$OC_2H_5]$—. If X is a radical —$(CH_3)C(R^4)$—, this can be, for example, —$(CH_3)CH$—, —$(CH_3)C(CH_3)$— or —$(CH_3)C(C_{12}H_{25})$—, and —$(CH_3)C(CH_3)$— is particularly preferred.

A —CH[—$CH_2$—CH($R^5$)($SR^6$)]— group X can be, for example, one of the radicals —CH[—$CH_2$—$CH_2$—$SCH_3$]—, —CH[—$CH_2$—CH($CH_3$)($SCH_3$)]—, —CH[—$CH_2$—$CH_2$—S—$CH_2$—CO—$OCH_3$]— or —CH[—$CH_2$—$CH_2$—S—$CH_2$—$CH_2$—CO—$OC_{18}H_{37}$]—.

A —CH[—$CH_2$—CH($R^5$)($SOR^6$)]— radical X can be, for example, a —CH[—$CH_2$—$CH_2$—$SOCH_3$]—, —CH[—$CH_2$—CH($CH_3$)—$SOCH_3$]—, —CH[—$CH_2$—$CH_2$—$SOCH_2$—CO—$OCH_3$]— or —CH[—$CH_2$—$CH_2$—$SOCH_2$—CO—$OC_{18}H_{37}$]— group.

A —CH[—$CH_2$—CH($R^5$)($SO_2R^6$)]— group X can be, for example, one of the groups —CH[—$CH_2$—$CH_2$—$SO_2CH_3$]—, —CH[—$CH_2$—CH($CH_3$)—$SO_2CH_3$]—, —CH[—$CH_2$—$CH_2$—$SO_2CH_2$—CO—$OCH_3$]— or —CH[—$CH_2$—$CH_2$—$SO_2CH_2$—CH($CH_3$)—CO—$OC_{18}H_{37}$]—.

A $C_1$–$C_{24}$-alkyl radical $R^3$ and a $C_1$–$C_{18}$-alkyl radical $R^6$ or $R^7$ can be, for example, methyl, ethyl, n-propyl, isopropyl, n-butyl, sec.-butyl, tert.-butyl, n-amyl, isoamyl, n-octyl, 1,1,3,3-tetramethylbutyl, n-decyl, n-dodecyl, n-tetradecyl, n-hexadecyl or n-octadecyl, and $R^3$ can additionally also be n-eicosyl, n-docosyl or n-tetracosyl. $R^3$, $R^6$ and $R^7$ are particularly preferably methyl.

A $C_1$–$C_8$-alkyl radical $R^8$ or $R^9$ can be, for example, methyl, ethyl, n-propyl, isopropyl, n-butyl, sec.-butyl, tert.-butyl, n-amyl, isoamyl, n-hexyl, 1,1,3,3-tetramethylbutyl or n-octyl. Methyl is preferred.

Preferred compounds of the formula I are those in which $R^1$ is $C_1$–$C_8$-alkyl, phenyl or $C_7$–$C_9$-aralkyl and X is one of the groups —$(CH_3)C[(CH_2)_m$—CO—$OR^3]$—, —$(CH_3)C(CH_3)$— or —$SO_2$—, in which $R^3$ is straight-chain or branched $C_1$—$C_{12}$-alkyl, and in which, finally, the bridge member B is a direct C—C bond, methylene, sulfide or disulfide and n can assume the value of a whole number from 0 to 10.

Compounds of the formula I which are also preferred are those in which $R^1$ is $C_1$–$C_8$-alkyl, phenyl or $C_7$–$C_9$-aralkyl and X is one of the groups —$(CH_3)C[—(CH_2)_m$—CO—$OR^3]$—, —$(CH_3)C(CH_3)$— or —$SO_2$—, in which $R^3$ is straight-chain or branched $C_1$–$C_{12}$-alkyl, and in which, finally, the bridge member B is a methylene, sulfide or disulfide group and n can assume the value of a whole number from 0 to 10.

Particularly preferred compounds of the formula I are those in which $R^1$ is tert.-butyl, $R^2$ is hydrogen and X is the group —$(CH_3)[—(CH_2)_m$—CO—$OR^3]$— or the group —$(CH_3)C(CH_3)$—, in which $R^3$ can be methyl or ethyl, and in which the bridge member B is a direct C—C bond or originates from the group consisting of methylene, sulfide and disulfide, and where n can assume the value of a whole number from 0 to 10.

Compounds of the formula I which are of interest are those in which X is a —$(CH_3)C[—(CH_2)_m$—CO—$OR^3]$— group, and in which $R^3$ is straight-chain or branched $C_1$–$C_{24}$-alkyl.

Compounds of the formula I which are also preferred are those in which X is a —(CH₃)C(R⁴)— group, and in The substances listed in the following table are representatives of compounds of the formula I:

(I)

| $R^1$ | $R^2$ | X | B | n |
|---|---|---|---|---|
| —CH₃ | —H | —(CH₃)CH— | direct bond | 0 |
| —C(CH₃)₃ | —H | —(CH₃)CH— | direct bond | 0 |
| —C₆H₅ | —H | —(CH₃)CH— | direct bond | 0 |
| —CH₂—C₆H₅ | —H | —(CH₃)CH— | direct bond | 0 |
| —C₆H₁₃ | —H | —(CH₃)CH— | direct bond | 0 |
| —C(CH₃)₃ | —CH₃ | —(CH₃)CH— | direct bond | 0 |
| —C(CH₃)₃ | —H | —(CH₃)C(CH₂—CO—OCH₃)— | direct bond | 0 |
| —C(CH₃)₃ | —H | —(CH₃)C(CH₂—CH₂—CO—OCH₃)— | direct bond | 0 |
| —C(CH₃)₃ | —H | —(CH₃)C(CH₂—CO—OC₁₆H₃₃) | direct bond | 0 |
| —C(CH₃)₃ | —H | —(CH₃)C(C₄H₉)— | direct bond | 0 |
| —C(CH₃)₃ | —H | —SO— | direct bond | 0 |
| —C(CH₃)₃ | —H | —SO₂— | direct bond | 0 |
| —C(CH₃)₃ | —H | —CH(CH₂—CH₂—SO₂—CH₃)— | direct bond | 0 |
| —C(CH₃)₃ | —H | —(CH₃)CH— | —CH₂— | 0 |
| —C(CH₃)₃ | —H | —(CH₃)CH— | —(CH₃)C(CH₃)— | 0 |
| —C(CH₃)₃ | —H | —(CH₃)CH— | —S— | 0 |
| —C(CH₃)₃ | —H | —(CH₃)CH— | —S—S— | 0 |
| —C(CH₃)₃ | —H | —(CH₃)CH— | direct bond | 2 |
| —C(CH₃)₃ | —H | —(CH₃)CH— | direct bond | 3 |
| —C(CH₃)₃ | —H | —(CH₃)C(CH₃)— | —S— | 6 |
| —C(CH₃)₃ | —H | —(CH₃)C(CH₃)— | direct bond | 0 |
| —C(CH₃)₃ | —H | —(CH₃)C(CH₂—CO—OCH₃)— | —S— | 5 | which $R^4$ is hydrogen or straight-chain $C_1$-$C_{12}$-alkyl, with the exception of ethyl.

Compounds of the formula I which are also of interest are those in which X is a —SO— group. Furthermore, preferred compounds of the formula I are those in which X is a —SO₂— group. Compounds of the formula I which deserve attention are also those in which X is a —CH[—CH₂—CH(R⁵)(SR⁶)— group, in which $R^5$ is hydrogen or methyl and $R^6$ is $C_1$-$C_{18}$-alkyl or a —(CH₂)$_t$—CO—OR⁷ group, in which $R^7$ is $C_1$-$C_{18}$-alkyl and the index t can assume the value 1 or 2.

Particularly preferred compounds of the formula I are those in which n assumes the value of a whole number from 1 to 10, but in particular from 2 to 10.

Compounds of the formula I which are additionally preferred are those in which the bridge member B is a group —(R⁸)C(R⁹)—, where $R^8$ and $R^9$ independently of one another are hydrogen, $C_1$-$C_8$-alkyl or phenyl.

Compounds of the formula I which are furthermore of interest are those in which the group B is a sulfide or disulfide bridge.

Compounds of the formula I which are also preferred are those in which $R^1$ is $C_1$-$C_{12}$-alkyl. Compounds of the formula I which furthermore deserve attention are those in which $R^1$ is phenyl or 1- or 2-naphthyl. Compounds of the formula I which are also of importance are those in which $R^1$ is $C_7$-$C_9$-aralkyl.

Compounds of the formula I which are furthermore of interest are those in which X is —(CH₃)C(CH₃)— and B is a direct C—C bond.

In the preparation of the compounds of the formula I, a monomeric phenolic component of the formula II

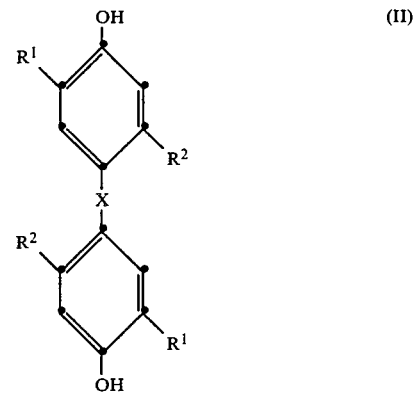

(II)

is used as the starting compound, and this is linked with various bridging reagents, depending on the nature of the bridge member B, or the compound of the formula II is coupled oxidatively to form direct C—C bonds.

Depending on the nature of the group —X—, the starting material II is prepared in various ways. The substitutents $R^1$, $R^2$, $R^3$, $R^4$, $R^5$, $R^6$, $R^7$, $R^8$ and $R^9$ are as defined above.

If —X— is a —(CH₃)C[(CH₂)$_m$—CO—OR³]— group, the procedure followed can be similar to that described in German Offenlegungsschrift No. 1,953,332, phenols, which may be unsubstituted or substituted, being condensed with ketocarboxylic acid esters of the formula $CH_3-CO-(CH_2)_m-CO-OR^3$ in the presence of hydrochloric acid and aliphatic mercaptans.

If $-X-$ is a group of the formula $-(CH_3)C(R^4)-$, substances of the formula II can be obtained in a manner which is known per se by condensation of phenols with aldehydes or ketones of the formula $CH_3-CO-R^4$.

The preparation of bisphenols of the formula II in which $-X-$ is a group $-CH[-CH_2-CH(R^5)(SR^6)]-$ is described in Swiss Patent Specification No. 476,775. Bisphenols of the formula II in which $-X-$ is a $-SO-$ or $-SO_2-$ group are prepared by oxidation of the corresponding sulfides with one or two molar proportions of hydrogen peroxide or m-chloroperbenzoic acid. The preparation of the sulfides is described in German Offenlegungsschrift No. 2,936,288.

Compounds of the formula II in which X is $-CH[-CH_2-CH(R^5)(SOR^6)]-$ or $-CH[-CH_2-CH(R^5)(SO_2R^6)]-$ are likewise prepared by oxidation of the sulfides with one or two molar proportions of hydrogen peroxide or m-chloroperbenzoic acid.

The compounds of the formula II are linked via a direct C—C bond by oxidative coupling. Various oxidising agents can be used here, for example tert.-butyl perbenzoate, dicumyl peroxide, benzoyl peroxide, copper-II salts and air or oxygen, hydrogen peroxide and sodium hydroxide, hydrogen peroxide and metal salts, such as $CuCl_2$, manganese-IV oxide or potassium hexacyanoferrate-III, at a pH value of 7, or Salcomine and air or oxygen. The preferred oxidising agent is potassium hexacyanoferrate-III or manganese-IV oxide. The oxidation is carried out in solution at temperatures between 0° to 140° C., but preferably between 25° C. and 110° C. Solvents which can be used are aliphatic or aromatic hydrocarbons, such as n-hexane, benzene, toluene or xylene, or chlorinated hydrocarbons, such as carbon tetrachloride, chloroform, methylene chloride or chlorobenzene. In certain cases, it is also possible to use a two-phase system consisting of hydrocarbon and water.

In a preferred embodiment, the compounds of the formula II are coupled with potassium hexacyanoferrate-III in a toluene/water system at temperatures between 50° C. and 85° C. The pH value of the aqueous phase is thereby kept at 7. The reaction time is about 15 hours.

In another preferred embodiment, the compounds of the formula II are coupled with manganese-IV oxide in toluene as the solvent. The reaction temperature here is 110° C. and the reaction time is about 12 hours.

If substances of the formula I are to contain a bridge $-B-=-(R^8)C(R^9)-$, bisphenols of the formula II are advantageously condensed with ketones or aldehydes $R^8-CO-R^9$ by reacting both reagents in solution under a nitrogen atmosphere, with addition of 1 to 20 mol % of a catalyst. Catalysts which can be used are mineral acids, such as sulfuric acid, Lewis acids, such as aluminium chloride, zinc chloride and boron trifluoride, and acid earths, such as Tonsil ®L 80S, Fulmont ®237 or Fulcat ®22B. Non-polar or polar organic solvents, for example n-hexane, ligroin, benzene, toluene, xylene, chlorobenzene, chlorinated methanes, chlorinated ethanes or dimethylformamide, can be used, depending on the solubility of the reactants or the temperature range at which the reaction is carried out. Depending on the reactivity of the starting compounds, the condensation is carried out in the temperature range from 0° C. to 180° C., but preferably between 5° C. and 115° C.

Compounds of the formula I in which the bridge $-B-$ is a $-S-$ or $-S-S-$ group are prepared in a similar manner. In this case, compounds of the formula II are used as starting substances and these are condensed with sulfur dichloride or disulfur dichloride as described above.

The molar ratios of phenolic component II to bridging reagent $R^8-CO-R^9$, $SCl_2$ or $S_2Cl_2$ can advantageously be varied between 1:2 and 2:1.

In a preferred embodiment, the compounds of the formula II are condensed with $SCl_2$ in toluene at temperatures between 0° C. and 5° C. The mixture is then allowed to after-react at 25° C. The reaction time in this variant is about 19 hours.

Linking of the monomeric bisphenols of the formula II as a rule gives mixtures of polymeric polyphenols. The invention thus also relates to mixtures of compounds of the formula I, which may contain unreacted starting material of the formula II.

The invention particularly relates to compositions of polyphenols containing the structural unit of the formula III

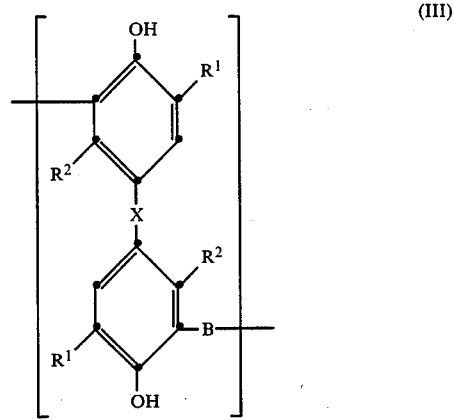

(III)

in which $R^1$, $R^2$, X and B are as defined above; the said compositions being obtainable by condensation of compounds of the formula II

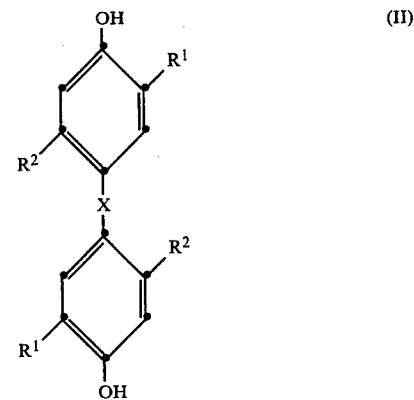

(II)

in which the radicals $R^1$, $R^2$ and X are as defined above, with a reagent which is capable of forming the bridge $-B-$.

Very particularly preferred compositions are those of polyphenols containing the structural unit of the formula III in which $R^1$ is tert.-butyl, $R^2$ is hydrogen, X is —(CH$_3$)C(CH$_3$)— and B is —S—, the average molecular weight of which $\overline{M}_n$ is 2,200.

Compositions which are also of interest are those containing the structural unit of the formula III in which $R^1$ is tert.-butyl, $R^2$ is hydrogen, X is —(CH$_3$)C(CH$_3$)— and B is a direct C—C bond, the average molecular weight $\overline{M}_n$ of which is 745.

Very particularly preferred compositions are those of polyphenols containing the structural unit of the formula III in which $R^1$ is tert.-butyl, $R^2$ is hydrogen, X is —(CH$_3$)C(CH$_2$—COOCH$_3$)— and B is —S—, the average molecular weight $\overline{M}_n$ of which is 1,900.

Compositions which furthermore deserve attention are those of polyphenols containing the structural unit of the formula III in which $R^1$ is tert.-butyl, $R^2$ is hydrogen, X is —(CH$_3$)C(CH$_2$—COOCH$_3$)— and B is a direct C—C bond, the average molecular weight $\overline{M}_n$ of which is 655.

The invention also relates to compositions containing an organic material which is sensitive to thermal, oxidative or radiation-induced degradation and at least one compound of the formula I.

In a preferred embodiment, the compositions according to the invention contain mixtures of compounds of the formula I.

In an embodiment which is also preferred, the compositions according to the invention contain mixtures of compounds of the formula I and unreacted starting material of the formula II.

Compositions which are likewise of interest are those in which the organic material is a polymer, in particular an elastomer.

Particularly preferred elastomers are: polydienes, for example polybutadiene, polyisoprene or polychloroprene; and block polymers, for example styrene/ethylene-propylene/styrene grades, styrene/butadiene/styrene or styrene/isoprene/styrene, as well as acrylonitrile/butadiene polymers.

These polymers can also be in the form of latices and can be stabilised as such.

Compositions which are furthermore preferred are those containing compounds of the formula I, or mixtures thereof, in which the bridge member —B— is —S—, and, as the organic substrate, ABS, IPS, polyethylene or an elastomer.

Compositions which are also preferred are those containing polypropylene and a compound of the formula I, or mixtures thereof, in which the bridge member —B— is a direct C—C bond. These compositions preferably also additionally contain starting material of the formula II and/or a thiosynergist.

The invention also relates to the use of compounds of the formula I for stabilising organic material against damage by the action of oxygen, heat, light or high-energy radiation.

The compounds are preferably used as antioxidants in organic polymers, especially in polyethylene, polypropylene or elastomers, or in mineral oils or synthetic oils.

Further examples of organic material which can advantageously be stabilised by the compounds according to the invention are:

1. Polymers of monoolefins and diolefins, for example polyethylene (which can be non-crosslinked or crosslinked), polypropylene, polyisobutylene, polybut-1-ene, polymethylpent-1-ene, polyisoprene or polybutadiene, and polymers of cycloolefins, for example of cyclopentene or norbornene.

2. Mixtures of the polymers mentioned under (1), for example mixtures of polypropylene and polyisobutylene.

3. Copolymers of monoolefins and diolefins with one another or with other vinyl monomers, for example ethylene/propylene copolymers, propylene/but-1-ene copolymers, propylene/isobutylene copolymers, ethylene/but-1-ene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and salts thereof (ionomers), as well as terpolymers of ethylene with propylene and a diene, such as hexadiene, dicyclopentadiene or ethylidenenorbornene.

4. Polystyrene and poly-(p-methylstyrene).

5. Copolymers of styrene or $\alpha$-methylstyrene with dienes or acrylic derivatives, for example styrene/butadiene, styrene/acrylonitrile, styrene/alkyl methacrylate, styrene/maleic anhydride and styrene/acrylonitrile/methyl acrylate; high impact strength mixtures of styrene copolymers and another polymer, for example a polyacrylate, a diene polymer or an ethylene/propylene/diene terpolymer; and block copolymers of styrene, for example styrene/butadiene/styrene, styrene/isoprene/styrene, styrene/(ethylene or butylene)/styrene or styrene/(ethylene or propylene)/styrene.

6. Graft copolymers of styrene, for example styrene on polybutadiene, styrene and acrylonitrile on polybutadiene, styrene and maleic anhydride on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and mixtures thereof with the copolymers mentioned under (5), for example those known as so-called ABS, MBS, ASA or AES polymers.

7. Halogen-containing polymers, for example polychloroprene, chlorinated rubber, chlorinated or chlorosulfonated polyethylene, epichlorohydrin homopolymers and copolymers and, in particular, polymers of halogen-containing vinyl compounds, for example polyvinyl chloride, polyvinylidene chloride, polyvinyl fluoride and polyvinylidene fluoride; and copolymers thereof, such as vinyl chloride/vinylidene chloride, vinyl chloride/vinyl acetate or vinylidene chloride/vinyl acetate.

8. Polymers which are derived from $\alpha,\beta$-unsaturated acids and derivatives thereof, such as polyacrylates and polymethacrylates, polyacrylamides and polyacrylonitriles.

9. Copolymers of the monomers mentioned under (8) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

10. Polymers which are derived from unsaturated alcohols and amines or acyl derivatives or acetals thereof, such as polyvinyl alcohol, polyvinyl acetate, stearate, benzoate or maleate, polyvinylbutyral, polyallyl phthalate or polyallylmelamine.

11. Homopolymers and copolymers of cyclic ethers, such as polyalkylene glycols, polyethylene oxide, polypropylene oxide or copolymers thereof with bisglycidyl ethers.

12. Polyacetals, such as polyoxymethylene, and those polyoxymethylenes which contain comonomers, for example ethylene oxide.

13. Polyphenyl oxides and sulfides and mixtures thereof with styrene polymers.

14. Polyurethanes which are derived from polyethers, polyesters and polybutadienes with terminal hydroxyl groups on the one hand and aliphatic or aromatic polyisocyanates on the other hand, and intermediates thereof.

15. Polyamides and copolyamides which are derived from diamines and dicarboxylic acids and/or aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide and poly-m-phenyleneisophthalamide, and block copolymers thereof with polyethers, for example with polyethylene glycol, polypropylene glycol or polytetramethylene glycol.

16. Polyureas, polyimides, polyamide-imides and polybenzimidazoles.

17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate and polyhydroxybenzoates, and block polyetheresters which are derived from polyethers with hydroxyl end groups.

18. Polycarbonates.

19. Polysulfones, polyether-sulfones and polyetherketones.

20. Crosslinked polymers which are derived from aldehydes on the one hand and phenols, urea or melamine on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols, and vinyl compounds, as crosslinking agents, as well as their halogen-containing, low-burning modifications.

23. Crosslinkable acrylic resins which are derived from substituted acrylic acid esters, for example from epoxy-acrylates, urethane-acrylates or polyester-acrylates.

24. Alkyd resins, polyester resins and acrylate resins which are crosslinked with melamine resins, urea resins, polyisocyanates or epoxy resins.

25. Crosslinked epoxy resins which are derived from polyepoxides, for example from bis-glycidyl ethers or from cycloaliphatic diepoxides.

26. Naturally occurring polymers, such as cellulose, natural rubber, gelatin and derivatives thereof which are chemically modified in a polymer-homologous manner, such as cellulose acetates, propionates and butyrates, and the cellulose ethers, such as methylcellulose.

27. Mixtures (polyblends) of the abovementioned polymers, for example EP/EPDM, polyamide 6/EPDM or ABS, PVC/EVA, PVC ABS, PVC/MBS, PC/ABS or PBTP/ABS.

28. Naturally occurring and synthetic organic substances which are pure monomeric compounds or mixtures thereof, for example mineral oils, animal or vegetable fats, oils and waxes or oils, waxes and fats based on synthetic esters (for example phthalates, adipates, phosphates or trimellitates), and mixtures of synthetic esters with mineral oils in any weight ratio, for example those used as spinning preparations, and aqueous emulsions thereof.

29. Aqueous emulsions of natural or synthetic rubbers, for example natural rubber latex or latices of carboxylated styrene/butadiene copolymers.

The stabilisers are added to the plastics in a concentration of 0.01-5% by weight, based on the material to be stabilised. Preferably, 0.1 to 2.0% by weight, and particularly preferably, 0.3 to 0.6% by weight, of the compounds, based on the material to be stabilised, are incorporated into this material.

The incorporation can be effected, for example, by mixing in the substances of the formula I and, if appropriate, other additives by the methods customary in the art, before or during shaping, or by application of the dissolved or dispersed compounds to the polymers, if necessary with subsequent evaporation of the solvent. The novel compounds can also be added to the plastics to be stabilised in the form of a masterbatch which contains these compounds, for example, in a concentration of 2.5 to 25% by weight.

In the case of crosslinked polyethylene, the compounds are added before the crosslinking.

The materials thus stabilised can be used in the most diverse form, for example as films, fibres, tapes, moulding compositions or profiles, or as binders for varnishes, adhesives or putty.

In practice, the polyphenols of the formula I can be used together with other stabilisers. Compounds of the formula I in which B is a direct C—C bond give highly active antioxidant mixtures in combination with the starting substances. All the products of the formula I exhibit a very powerful synergism with co-stabilisers, for example with dilauryl thiodipropionate (DLDP) or distearyl thiodipropionate (DSTDP). The present invention thus also relates to the organic materials which are stabilised by the addition of 0.01 to 5% by weight of polyphenols of the formula I and, if appropriate, may also contain other additives.

Particularly preferred stabilisers for organic material are compounds of the formula I or mixtures of compounds of the formula I in which B is a direct C—C bond in combination with thiosynergists, in particular in combination with distearyl esters of β-thiodipropionic acid (DSTDP), dilauryl esters of β-thiodipropionic acid (DLDP) or pentaerythritol tetrakis-(β-dodecylmercapto)-propionate. ABS is the particularly preferred organic substrate.

Examples of other additives which can be used together with the stabilisers employed according to the invention are:

1.

Antioxidants 1.1. Alkylated monophenols: 2,6-di-tert.-butyl-4-methylphenol, 2-tert.-butyl-4,6-dimethylphenol, 2,6-di-tert.-butyl-4-ethylphenol, 2,6-di-tert.-butyl-4-n-butylphenol, 2,6-di-tert.-butyl-4-i-butylphenol, 2,6-di-cyclopentyl-4-methylphenol, 2-(α-methylcyclohexyl)-4,6-dimethylphenol, 2,6-di-octadecyl-4-methylphenol, 2,4,6-tri-cyclohexylphenol and 2,6-di-tert.-butyl-4-methoxymethylphenol;

1.2. Alkylated hydroquinones: 2,6-di-tert.-butyl-4-methoxyphenol, 2,5-di-tert.-butyl-hydroquinone, 2,5-ditert.-amylhydroquinone and 2,6-diphenyl-4-octadecyloxyphenol;

1.3. Hydroxylated thiodiphenyl ethers: 2,2'-thio-bis-(6-tert.-butyl-4-methylphenol), 2,2'-thio-bis-(4-octylphenol), 4,4'-thio-bis-(6-tert.-butyl-3-methylphenol) and 4,4'-thio-bis-(6-tert.-butyl-2-methylphenol);

1.4. Alkylidene-bisphenols: 2,2'-methylene-bis-(6-tert.-butyl-4-methylphenol), 2,2'-methylene-bis-(6-tert.-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert.-butylphenol), 2,2'-ethylidene-bis-(4,6-di-tert.-butylphenol), 2,2'-ethylidene-bis-(6-tert.-butyl-4-isobutylphenol), 2,2'-methylene-bis-[6-(α-methylbenzyl)-4-nonylphenol], 2,2'-methylene-bis-[6-(α,α-dimethylbenzyl)-4-nonylphenyl], 4,4'-methylene-bis-(2,6-di-tert.-butylphenol), 4,4'-methylene-bis-(6-tert.-butyl-2-methylphenol), 1,1-bis-(5-tert.-butyl-4-hydroxy-2-methylphenyl)butane, 2,6-di-(3-tert.-butyl-5-methyl-2-hydroxybenzyl)-4-methylphenol, 1,1,3-tris-(5-tert.-butyl-4-hydroxy-2-methylphenyl)-butane, 1,1-bis-(5-tert.-butyl-4-hydroxy-2-methylphenyl)-3-n-dodecylmercaptobutane, ethylene glycol bis-[3,3-bis-(3'-tert.-butyl-4'-hydroxyphenyl)-butyrate], di-(3-tert.-butyl-4-hydroxy-5-methylphenyl)-dicyclopentadiene and di-[2-(3'-tert.-butyl-2'-hydroxy-5'-methyl-benzyl)-6-tert.-butyl-4-methyl-phenyl]terephthalate;

1.5. Benzyl compounds: 1,3,5-tri-(3,5-di-tert.-butyl-4-hydroxybenzyl)-2,4,6-trimethylbenzene, di-(3,5-di-tert.-butyl-4-hydroxybenzyl)sulfide, isooctyl 3,5-di-tert.-butyl-4-hydroxybenzyl-mercaptoacetate, bis-(4-tert.-butyl-3-hydroxy-2,6-dimethylbenzyl)dithiol-terephthalate, 1,3,5-tris-(3,5-di-tert.-butyl-4-hydroxybenzyl)isocyanurate, 1,3,5-tris-(4-tert.-butyl-3-hydroxy-2,6-dimethylbenzyl)isocyanurate, di-octadecyl 3,5-di-tert.-butyl-4-hydroxybenzylphosphonate and the calcium salt of monoethyl 3,5-di-tert.-butyl-4-hydroxybenzylphosphonate;

1.6. Acylaminophenols: 4-hydroxy-lauric acid anilide, 4-hydroxy-stearic acid anilide, 2,4-bis-octylmercapto-6-(3,5-di-tert.-butyl-4-hydroxyanilino)-s-triazine and octyl N-(3,5-di-tert.-butyl-4-hydroxyphenyl)-carbamate;

1.7. Esters of β-(3,5-di-tert.-butyl-4-hydroxyphenyl)-propionic acid with monohydric or polyhydric alcohols: for example with methanol, octadecanol, hexane-1,6-diol, neopentylglycol, thiodiethylene glycol, diethylene glycol, triethylene glycol, pentaerythritol, tris-hydroxyethyl isocyanurate or di-hydroxyethyl-oxalic acid diamide;

1.8 Esters of β-(5-tert.-butyl-4-hydroxy-3-methylphenyl)propionic acid with monohydric or polyhydric alcohols: for example with methanol, octadecanol, hexane-1,6-diol, neopentylglycol, thiodiethylene glycol, diethylene glycol, triethylene glycol, pentaerythritol, tris-hydroxyethyl isocyanurate or di-hydroxyethyl-oxalic acid diamide; and 1.9. Amides of β-(3,5-di-tert.-butyl-4-hydroxyphenyl)propionic acid: for example N,N'-di-(3,5-di-tert.-butyl-4-hydroxyphenylpropionyl)-hexamethylenediamine, N,N'-di-(3,5-di-tert.-butyl-4-hydroxyphenylpropionyl)-trimethylenediamine and N,N'-di-(3,5-di-tert.-butyl-4-hydroxyphenylpropionyl)hydrazine.

2. UV absorbers and light stabilisers

2.1. 2-(2'-Hydroxyphenyl)-benzotriazoles: for example the 5'-methyl, 3',5'-di-tert.-butyl, 5'-tert.-butyl, 5'-(1,1,3,3-tetramethylbutyl), 5-chloro-3',5'-di-tert.-butyl, 5-chloro-3'-tert.-butyl-5'-methyl, 3'-sec.-butyl-5'-tert.-butyl, 4'-octoxy, 3',5'-di-tert.-amyl or 3',5'-bis-(α,α-dimethylbenzyl)derivative;

2.2. 2-Hydroxybenzophenones: for example the 4-hydroxy, 4-methoxy, 4-octoxy, 4-decyloxy, 4-dodecyloxy, 4-benzyloxy, 4,2',4'-trihydroxy or 2'-hydroxy-4,4'-dimethoxy derivative;

2.3 esters of unsubstituted or substituted benzoic acids: for example 4-tert.-butyl-phenyl salicylate, phenyl salicylate, octylphenyl salicylate, dibenzoylresorcinol, bis-(4-tert.-butylbenzoyl)-resorcinol, benzoylresorcinol, 2,4-di-tert.-butylphenyl 3,5-di-tert.-butyl-4-hydroxybenzoate and hexadecyl 3,5-di-tert.-butyl-4-hydroxybenzoate;

2.4. Acrylates: for example ethyl or isooctyl α-cyano-β,β-diphenylacrylate, methyl α-carbomethoxy-cinnamate, methyl or butyl α-cyano-β-methyl-p-methoxy-cinnamate, methyl α-carbomethoxy-p-methoxy-cinnamate and N-(β-carbomethoxy-β-cyanovinyl)-2-methyl-indoline;

2.5. Nickel compounds: for example nickel complexes of 2,2'-thio-bis-[4-(1,1,3,3-tetramethylbutyl)-phenol], such as the 1:1 or 1:2 complex, with or without additional ligands, such as n-butylamine, triethanolamine or N-cyclohexyl-diethanolamine, nickel dibutyl-dithiocarbamate, nickel salts of 4-hydroxy-3,5-di-tert.-butylbenzyl-phosphonic acid monoalkyl esters, such as the methyl or ethyl ester, nickel complexes of ketoximes, such as of 2-hydroxy-4-methyl-phenyl undecyl ketone oxime, and nickel complexes of 1-phenyl-4-lauroyl-5-hydroxy-pyrazole, with or without additional ligands;

2.6. Sterically hindered amines: for example bis-(2,2,6,6-tetramethylpiperidiyl)sebacate, bis-(1,2,2,6,6-pentamethylpiperidyl)sebacate, bis-(1,2,2,6,6-pentamethylpiperidyl)n-butyl-3,5-di-tert.-butyl-4-hydroxybenzyl-malonate, the condensation product of 1-hydroxyethyl-2,2,6,6-tetramethyl-4-hydroxypiperidine and succinic acid, the condensation product of N,N'-(2,2,6,6-tetramethyl-4-piperidyl)-hexamethylenediamine and 4-tert.-octylamino-2,6-dichloro-1,3,5-s-triazine, tris-(2,2,6,6-tetramethyl-4-piperidyl)nitrilotriacetate, tetrakis-(2,2,6,6-tetramethyl-4-piperidyl)-1,2,3,4-butane-tetracarboxylic acid and 1,1'-(1,2-ethanediyl)-bis-(3,3,5,5-tetramethyl-piperazinone); and 2.7. Oxalic acid diamides: for example 4,4'-di-octyloxyoxanilide, 2,2'-di-octyloxy-5,5'-di-tert.-butyl-oxanilide, 2,2'-di-dodecyloxy-5,5'-di-tert.-butyl-oxanilide, 2-ethoxy-2'-ethyl-oxanilide, N,N'-bis-(3-dimethylaminopropyl)-oxalamide, 2-ethoxy-5-tert.-butyl-2'-ethyloxanilide and its mixture with 2-ethoxy-2'-ethyl-5,4'-di-tert.-butyl-oxanilide, and mixtures of ortho- and para-methoxy- and of o- and p-ethoxy-disubstituted oxanilides.

3. Metal deactivators: for example N,N'-diphenyloxalic acid diamide, N-salicylal-N'-salicyloylhydrazine, N,N'-bis-salicyloylhydrazine, N,N'-bis-(3,5-di-tert.-butyl-4-hydroxyphenylpropionyl)-hydrazine, 3-salicyloylamino-1,2,4-triazole and bis-benzylidene-oxalic acid dihydrazide.

4. Phosphites and phosphonites: for example triphenyl phosphite, diphenyl alkyl phosphites, phenyl dialkyl phosphites, tri-(nonylphenyl)phosphite, trilauryl phosphite, trioctadecyl phosphite, distearyl-pentaerythritol diphosphite, tris-(2,4-di-tert.-butylphenyl)-phosphite, diisodecyl-pentaerythritol diphosphite, di-(2,4-di-tert.-butylphenyl)-pentaerythritol diphosphite, tristearyl sorbitol triphosphite and tetrakis-(2,4-di-tert.-butylphenyl)-4,4′-biphenylene diphosphonite.

5. Compounds which destroy peroxide: for example esters of β-thio-dipropionic acid, for example the lauryl, stearyl, myristyl or tridecyl ester, mercaptobenzimidazole, the zinc salt of 2-mercaptobenzimidazole, zinc dibutyl-dithiocarbamate, dioctadecyl disulfide and pentaerythritol tetrakis-(β-dodecylmercapto)-propionate.

6. Polyamide stabilisers: for example copper salts in combination with iodides and/or phosphorus compounds and salts of divalent manganese.

7. Basic co-stabilisers: for example melamine, polyvinylpyrrolidone, dicyandiamide, triallyl cyanurate, urea derivatives, hydrazine derivatives, amines, polyamides, polyurethanes and alkali metal and alkaline earth metal salts of higher fatty acids, for example Ca stearate, Zn stearate, Mg stearate, Na ricinoleate, K palmitate, antimony pyrocatecholate or tin pyrocatecholate.

8. Nucleating agents: for example 4-tert.-butylbenzoic acid, adipic acid and diphenylacetic acid.

9. Fillers and reinforcing agents: for example calcium carbonate, silicates, glass fibres, asbestos, talc, kaolin, mica, barium sulfate, metal oxides and hydroxides, carbon black and graphite.

10. Other additives: for example plasticisers, lubricants, emulsifiers, pigments, optical brighteners, flameproofing agents, antistatics and blowing agents.

EXAMPLE 1

Condensation of 2,2-bis-(3-tert.-butyl-4-hydroxyphenyl)-propane with sulfur dichloride (stabiliser 1)

102.1 g (0.3 mole) of 2,2-bis-(3-tert.-butyl-4-hydroxyphenyl)-propane are introduced into 300 ml of toluene and the solution is cooled to 5° C. and to 0° C. A solution of 19 ml (0.3 mole) of $SCl_2$ in 150 ml of toluene is added dropwise at this temperature in the course of 4 hours. The reaction is exothermic and HCl is detached. The mixture is then warmed to room temperature and kept there for 15 hours. The reaction solution is subsequently washed neutral three times with in each case 200 ml of water in a separating funnel, dried over $Na_2SO_4$ and filtered. The filtrate is concentrated on a rotary evaporator and the residue is dried under a high vacuum at 60° C. for 2 hours. 107.4 g of a slightly yellowish powder with a melting point of about 60° C. are obtained (stabiliser 1). The substance is purified by means of medium-pressure chromatography (toluene as the solvent) and the molecular weight of the individual fractions is determined by mass spectroscopy. Fractions with molecular weights of 710, 1,080 and 1,480 are obtained.

The product thus corresponds to a mixture of compounds of the formula I in which $R^1$ is tert.-butyl, $R^2$ is hydrogen, X is —(CH$_3$)C(CH$_3$)—, B is —S— and n is 0, 1 and 2.

EXAMPLE 2

Oxidative coupling of ethyl 3,3-bis-(3-tert.-butyl-4-hydroxyphenyl)-butanoate (stabiliser 2)

41.3 g (0.1 mole) of ethyl 3,3-bis-(3-tert.-butyl-4-hydroxyphenyl)-butanoate are introduced into 150 ml of toluene and the mixture is heated up to 50° C. A solution of 43.8 g (0.13 mole) of potassium hexacyanoferrate-III in 200 ml of water is now added dropwise in the course of 3 hours, during which the pH value is kept at 7 by addition of $NaHCO_3$. The mixture is heated up to 85° C. and kept at this temperature for 15 hours.

The organic phase is then separated off in a separating funnel, washed four times with 200 ml of water each time, dried over 20 g of $Na_2SO_4$ and concentrated on a rotary evaporator. The residue is dried under a high vacuum at 60° C. for 2 hours.

40.3 g (98.3% of theory) of a slightly yellowish powder which has a melting point of about 100° C., consists of 75.7% of C and 8.6% of H and has an average molecular weight $\overline{M}_n$ of 890 (determined by vapour pressure osmometry) are obtained.

EXAMPLE 3

Oxidative coupling of ethyl 3,3-bis-(3-tert.-butyl-4-hydroxyphenyl)-butanoate (stabiliser 3)

20.6 g (0.05 mole) of ethyl 3,3-bis-(3-tert.-butyl-4-hydroxyphenyl)-butanoate and 9.7 g (0.1 mole) of manganese-IV oxide are introduced into 200 ml of toluene and the mixture is refluxed for 12 hours. After cooling to room temperature, the solid residue is filtered off and the filtrate is washed twice with 200 ml of water each time. The organic phase is dried over 20 g of $Na_2SO_4$ and clarified with 5 g of Prolith-Rapid (bleaching earth). After filtration, the filtrate is concentrated on a rotary evaporator and the residue is dried under a high vacuum at 60° C. for 2 hours.

19.3 g (94.2% of theory) of an orange powder which has a melting point of about 80° C., consists of 76.0% of C and 9.2% of H and has an average molecular weight $\overline{M}_n$ of 540 (determined by vapour pressure osmometry) are obtained.

EXAMPLE 4

Condensation of ethyl 3,3-bis-(3-tert.-butyl-4-hydroxyphenyl)-butanoate with sulfur dichloride (stabiliser 4)

The condensation is carried out as described in Example 1. A slightly yellow product which has a melting point of about 100° C. and an average molecular weight $\overline{M}_n$ of 1,900 (determined by vapour pressure osmometry) is obtained.

EXAMPLE 5

Oxidative coupling of 2,2-bis-(3-tert.-butyl-4-hydroxyphenyl)-propane (stabiliser 5)

The reaction is carried out as described in Example 2, using potassium hexacyanoferrate-III. A yellow product which has a melting point of about 95° C. and an average molecular weight $\overline{M}_n$ of 745 (determined by vapour pressure osmometry) is obtained.

EXAMPLE 6

Stabiliser action in ABS 100 parts by weight of non-stabilised ABS powder are mixed with the various stabilisers shown in Tables I and II.

The resulting mixtures are compounded on a two-roll mill at a maximum of 170° C. for 5 minutes and the hides are then drawn off. The crude hides are pressed on a hydraulic laboratory press at 180° C. for 6 minutes to give sheets 1 mm thick, from which test pieces 50×20 mm in dimensions are stamped.

The effectiveness of the stabilisers added to the test pieces is tested by heat-ageing in a circulating air oven at 180° C. The infrared absorption spectrum of the surface, obtained by reflection spectroscopy (ATR), serves as a criterion for the damage (oxidation) which occurs during ageing. In particular, the increase in the carbonyl extinction (1720 cm$^{-1}$) as a function of time is monitored and compared with an absorption band which remains constant (1455 cm$^{-1}$). A measure of the degradation is thus:

$$V = \frac{\text{optical density at 1720 cm}^{-1} (>C=O)}{\text{optical density at 1455 cm}^{-1} (>CH_2)}$$

The time after which V reaches the value 0.1 ($t_{0.1}$) is chosen at the arbitrary end point.

In addition, the Yellowness Index (YI) of the samples as a function of time is measured.

TABLE 1

| Stabiliser according to Preparation Example No. 0.25% by weight | Testing in ABS | | | | | | |
|---|---|---|---|---|---|---|---|
| | OVEN AGEING AT 180° C. | | | | | | |
| | $t_{0.1}$ (minutes) | Y.I. ASTM D 1925 after oven ageing for | | | | | |
| | | 12' | 15' | 30' | 45' | 60' | 90' |
| 1 | 29' | 17.3 | 26 | 33 | 56 | 69 | 80 |
| 4 | 52' | 17.6 | 24 | 32 | 32 | 48 | 73 |
| no stabiliser | 7' | 14.7 | 37 | 56 | 69 | 80 | 87 |

TABLE II

| Stabiliser according to Preparation Example No. + DLTDP 0.25% by weight of stabiliser 0.5% by weight of DLTDP | Testing in ABS with the synergist DLTDP (dilauryl thiodipropionate). | | | | | | |
|---|---|---|---|---|---|---|---|
| | OVEN AGEING AT 180° C. | | | | | | |
| | $t_{0.1}$ (minutes) | Y.I. ASTM D 1925 after oven ageing for | | | | | |
| | | 12' | 15' | 30' | 45' | 60' | 90' |
| 1 | 116' | 16.1 | 23 | 24 | 28 | 31 | 34 |
| 4 | 119' | 17.1 | 22 | 24 | 26 | 28 | 32 |
| no stabiliser | 7' | 14.7 | 37 | 56 | 69 | 80 | 87 |

EXAMPLE 7 stabiliser action in high impact polystyrene

High impact polystyrene containing 8% by weight of polybutadiene (high cis content) and 0.035% by weight of 2,6-di-tert.-butyl-p-cresol, as a basic stabiliser, 0.05% by weight of zinc stearate, as a lubricant, and 0.1% by weight of one of the antioxidants according to the invention (in each case designated with the number of the corresponding preparation example in the following Table III) is extruded twice at 220° C. and the resulting granules are pressed at 185° C. for 3 minutes to test platelets 2 mm thick.

The test pieces are subjected to oven-ageing in a circulating air oven, and the Yellowness Index according to ASTM D 1925 at 80° C. (measurement of the test pieces after 0, 250, 500, 750 and 1,000 hours) and at 160° C. (measurement of the test pieces after 0, 60, 90, 120 and 180 minutes) is determined. The results are shown in Table III.

TABLE III

| Stabiliser according to Preparation Example No. | Y.I. at 80° C. after (in hours) | | | | | Y.I. at 160° C. after (in minutes) | | | | |
|---|---|---|---|---|---|---|---|---|---|---|
| | 0 | 250 | 500 | 750 | 1000 | 0 | 60 | 90 | 120 | 180 |
| no antioxidant | 1 | 13 | 17 | 18 | 28 | 1 | 22 | 51 | 69 | 86 |
| 1 | 7 | 16 | 19 | 19 | 24 | 7 | 15 | 21 | 26 | 33 |
| 4 | 6 | 14 | 21 | 24 | 28 | 6 | 15 | 22 | 24 | 30 | cl EXAMPLE 8

Stabiliser action in polypropylene 100 parts of polypropylene (melt flow index of 2.6 g/10 minutes, 230° C./2,160 g) are intensively mixed with 0.2 part of one of the additives listed in the following Table IV in a shaking apparatus for 10 minutes.

The resulting mixture is kneaded in a Brabender Plastograph at 200° C. for 10 minutes and the mass obtained in this manner is then pressed in a plate press at a plate temperature of 260° C. to sheets 1 mm thick, from which strips 1 cm wide and 17 cm long are stamped.

The effectiveness of the additives added to the test strips is tested by heat-ageing in a circulating air oven at 135° and 149° C., an additive-free test strip being used for comparison. 3 test strips of each formulation are used. The incipient decomposition of the test strip, which is easily recognisable by complete embrittlement, is defined as the end point. The results are given in days.

TABLE IV

| | Days to incipient decomposition | |
|---|---|---|
| Stabiliser No. | 135° C. | 149° C. |
| no additive | 1 | <1 |
| 2 | 28 | 6 |
| 5 | 77 | 17 |

EXAMPLE 9

Stabiliser action in polypropylene in the presence of a thiosynergist 100 parts of polypropylene (melt flow index 2.6 g/10 minutes, 230° C./2,160 g) are intensively mixed with 0.1 part of one of the additives shown in the following Table V and 0.3 part of dilauryl thiodipropionate in a shaking apparatus for 10 minutes; the procedure is otherwise as in Example 8. A test strip containing only 0.3 part of dilauryl dithiodipropionate is used for comparison.

TABLE V

| | Days to incipient decomposition | |
|---|---|---|
| Stabiliser No. | 135° C. | 149° C. |
| no additive | 16 | 2 |
| 2 | 176 | 78 |
| 5 | 205 | 48 |

EXAMPLE 10

Resistance to extraction of a polypropylene stabilised according to the invention 100 parts by weight of non-stabilised PP powder (Propathene ® HF 20) are mixed with the various stabilisers shown in Table VI. The resulting mixture is kneaded in a Brabender Plastograph at 200° C. for 10 minutes and the mass obtained in this manner is then pressed in a plate press at a plate temperature of 260° C. to sheets 1 mm thick, from which strips 1 cm wide and 17 cm long are stamped. The strips (weighted with a stainless steel screw) are introduced into a vessel of distilled water, the weight ratio of PP: water being 1:50. The vessel is placed for 6, 12 or 18 weeks in an oven regulated at 90° C. After this water treatment, the samples are subjected to an oven-ageing test at 135° C. and 149° C. in a circulating air oven. The incipient decomposition of the test strip, which is easily recognisable by complete embrittlement, is defined as the end point. The results are given in days. A sample which has not undergone water treatment is used for comparison.

TABLE VI

| Additive (% by weight) | Stabiliser No. 2 (0.1) | + | DSTDP (0.3) | + | Ca stearate (0.1) |
|---|---|---|---|---|---|
| Water treatment before oven ageing (weeks) | 0 | | 6 | | 12 | 18 |
| Days to incipient decomposition (oven ageing at 135° C.) | 176 | | 161 | | 155 | 153 |
| Days to incipient decomposition (oven ageing at 149° C.) | 78 | | 70 | | 61 | 50 |

What is claimed is:

1. A compound of formula I

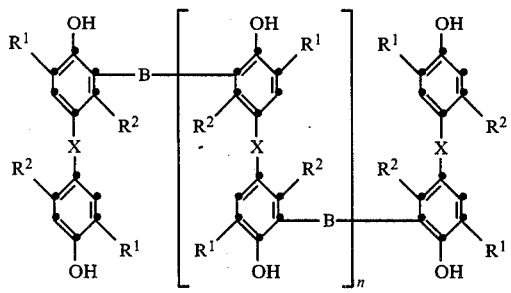

(I)

in which $R^1$ is $C_1$-$C_{12}$-alkyl, $C_5$-$C_7$-cycloalkyl, phenyl, 1-naphthyl, 2-naphthyl or $C_7$-$C_9$-aralkyl, $R^2$ is hydrogen, X is —$(CH_3)C[-(CH_2)_m-CO-OR^3]$—, —CH[—$CH_2$—CH($R^5$)(SO—$R^6$)]— or —CH[—$CH_2$—CH($R^5$) ($SO_2$—$R^6$)]—, in which $R^3$ is straight-chain or branched $C_1$—$C_{24}$-alkyl, m is 1 or 2 and $R^5$ is hydrogen or methyl, and in which $R^6$ is straight-chain or branched $C_1$-$C_{18}$-alkyl or a group —$(CH_2)_t$—CO—$OR^7$, in which t is 1 or 2 and $R^7$ is straight-chain or branched $C_1$-$C_{18}$-alkyl, and in which B is a direct C—C bond or is —S— or —S—S—, and in which n is a whole number from 0 to 50.

2. A compound according to claim 1 in which $R^1$ is $C_1$-$C_8$-alkyl, phenyl or $C_7$-$C_9$-aralkyl, X is —$(CH_3)C[-(CH_2)_m-CO-OR^3]$—, in which $R^3$ is straight-chain or branched $C_1$-$C_{12}$-alkyl, and in which B is a direct C—C bond or is —S— or —S—S—, and where n is a whole number from 0 to 10.

3. A compound according to claim 1 in which $R^1$ is $C_1$-$C_8$-alkyl, phenyl or $C_7$-$C_9$-aralkyl, X is —$(CH_3)C[-(CH_2)_m-CO-OR^3]$—, in which $R^3$ is straight-chain or branched $C_1$-$C_{12}$-alkyl, and in which B is —S— or —S—S—, and where n is a whole number from 0 to 10.

4. A compound according to claim 1 in which $R^1$ is tert.-butyl, $R^2$ is hydrogen, X is —$(CH_3)C[-(CH_2)_m-CO-OR^3]$—, in which $R^3$ can be methyl or ethyl, and in which B is a direct C—C bond or is —S— or —S—S—, and where n is a whole number from 0 to 10.

5. A composition according to claim 4 which contains a mixture of compounds of formula I.

6. A composition according to claim 5 which additionally contains some material of formula II

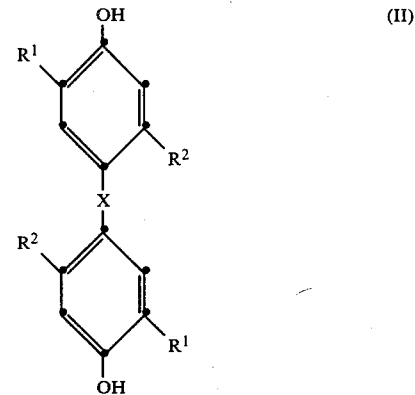

(II)

in which $R^1$ is $C_1$-$C_{12}$-alkyl, $C_5$-$C_7$-cycloalkyl, phenyl, 1-naphthyl, 2-naphthyl or $C_7$-$C_9$-aralkyl, $R^2$ is hydrogen, X is —$(CH_3)C[-(CH_2)_m-CO-OR^3]$—, —CH[—$CH_2$—CH($R^5$)(SO—$R^6$)]— or —CH[—$CH_2$—CH($R^5$) ($SO_2$—$R^6$)]—, in which $R^3$ is straight-chain or branched $C_1$-$C_{24}$-alkyl, m is 1 or 2 and $R^5$ is hydrogen or methyl, and in which $R^6$ is straight-chain or branched $C_1$-$C_{18}$-alkyl or a group —$(CH_2)_t$—CO—$OR^7$, in which t is 1 or 2 and $R^7$ is straight-chain or branched $C_1$-$C_{18}$-alkyl.

7. A compound according to claim 1 of the formula I, in which X is a —$(CH_3)C[-(CH_2)_m-CO-OR^3]$— group, and in which $R^3$ is straight-chain or branched $C_1$-$C_{24}$-alkyl.

8. A compound according to claim 1 of the formula I, in which B is a direct C—C bond.

9. A compound according to claim 1 of the formula I, in which the group B is a —S— or —S—S—.

10. A compound according to claim 1 of the formula I, in which $R^1$ is $C_1$-$C_{12}$-alkyl.

11. A compound according to claim 1 of the formula I, in which $R^1$ is tert.-butyl, $R^2$ is hydrogen, X is —$(CH_3)C(CH_2-COOCH_3)$— and B is —S— and which has an average molecular weight $\overline{M}_n$ of 1,900.

12. A compound according to claim 1 of the formula I, in which $R^1$ is tert.-butyl, $R^2$ is hydrogen, X is —$(CH_3)C(CH_2-COOCH_3)$— and B is a direct C—C bond and which has an average molecular weight $\overline{M}_n$ of 655.

13. A composition comprising an organic material selected from the group consisting of naturally occuring polymers, synthetic polymers, and animal and vegetable fats, waxes and oils and as a stabilizer against thermal, oxidative or ultra violet light degradation, an effective amount of at least one compound of the formula I according to claim 1.

14. A composition according to claim 13, containing compounds of the formula I in which B is a direct C—C bond and additionally containing at least one thiosynergist.

15. A composition according to claim 14, in which the organic material is acrylonitrile-butadiene-styrene copolymers.

16. A method of stabilizing an organic material against damage by the action of oxygen, heat, light or high-energy radiation which comprises incorporating in said material an effective amount of a compound according to claim 1.

* * * * *